United States Patent

Van Thillo et al.

(10) Patent No.: US 6,780,576 B1
(45) Date of Patent: Aug. 24, 2004

(54) SURFACTANTS

(75) Inventors: Etienne Van Thillo, Essen (BE); Johan Loccufier, Zwijnaarde (BE); Hartwig Andries, Rupelmonde (BE)

(73) Assignee: Agfa-Gevaert, Mortsel (BE)

( * ) Notice: Subject to any disclaimer, the term of this patent is extended or adjusted under 35 U.S.C. 154(b) by 0 days.

(21) Appl. No.: 10/601,788

(22) Filed: Jun. 23, 2003

(30) Foreign Application Priority Data

Jun. 6, 2003 (EP) .............................................. 03101661

(51) Int. Cl.⁷ ............................. G03C 1/38; G03C 1/91; C07D 235/28
(52) U.S. Cl. ....................... 430/523; 430/535; 430/536; 430/537; 430/636; 548/307.1
(58) Field of Search ................................ 430/523, 537, 430/535, 536, 636; 548/307.1

(56) References Cited

U.S. PATENT DOCUMENTS 3,704,130 A * 11/1972 Pollet et al.
4,639,408 A * 1/1987 Kitaguchi et al. .......... 430/351

* cited by examiner

*Primary Examiner*—Richard L. Schilling
(74) *Attorney, Agent, or Firm*—Leydig, Voit & Mayer, Ltd.

(57) ABSTRACT

A compound represented by formula (I):

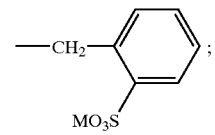

a compound represented by (II):

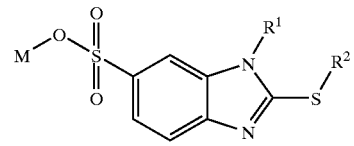

or a mixture of at least one compound represented by formula (I) with at least one compound represented by formula (II), wherein M is hydrogen, an alkali atom or an ammonium group; $R^1$ is hydrogen, a $-(CH_2)_m SO_3 M$ group or a

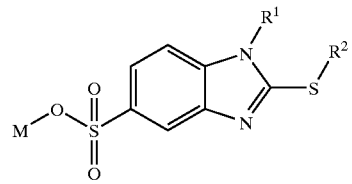

$R^2$ is an alkyl-, alkenyl- or alkynyl- group having 6 to 25 carbon atoms; and m is an integer between 1 and 5; the use of at least one compound represented by the above-mentioned formula (I), at least one compound represented by the above-mentioned formula (II) or a mixture of at least one compound represented by the above-mentioned formula (I) and at least one compound represented by the above-mentioned formula (II) as a surfactant; and a photographic material comprising a support and a layer containing photosensitive silver halide, characterized in that the photographic material contains at least one compound represented by the above-mentioned formula (I), at least one compound represented by the above-mentioned formula (II) or a mixture of at least one compound represented by the above-mentioned formula (I) and at least one compound represented by the above-mentioned formula (II).

3 Claims, No Drawings

SURFACTANTS

FIELD OF THE INVENTION

The present invention concerns 2-thioalkyl-benzimidazole-5-sulphonic acid and 2-thioalkyl-benzimidazole-6-sulphonic acid compounds and their use as surfactants.

BACKGROUND OF THE INVENTION

U.S. Pat. No. 2,053,822 discloses a process for the manufacture of sulphonic acids, consisting in treating with sulphonating agents imidazole derivatives having the atom grouping

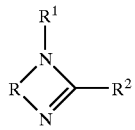

in which R represents a carbocyclic aromatic radical containing at the most 10 carbon atoms, $R_1$ represents an alkyl radical containing at least 7 carbon atoms and $R_2$ is a member selected from the group consisting of hydrogen and alkyl. None of the alkylating agents cited contains an aromatic group i.e. benzyl chloride is apparently not included. The aromatic nucleus R may comprise substituents, for example, sulpho groups. The 2-substituent may also be a methoxy-, ethoxy-, mercapto- or thioalkyl-group. U.S. Pat. No. 2,053,822 further discloses that new imidazoles are characterized by the atom grouping

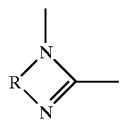

wherein the radical R represents a sulphonated aromatic radical, wherein further the nature of the μ-substituent follows from the above enumerations, and wherein at least one of the two nitrogen atoms is linked with a radical $R_1$. The examples disclose the reaction of dodecyl chloride, 2-chloroacetic acid dodecyl ester with μ-heptadecyl-benzimidazole followed by sulphonation.

Thermography is an image-forming process including a heating step and hence includes photothermography in which the image-forming process includes image-wise exposure and direct thermal processes in which the image-forming process includes an image-wise heating step. In direct thermal printing a visible image pattern is produced by image-wise heating of a recording material.

U.S. Pat. No. 3,704,130 discloses a method of preparing a photographic fine-grain silver halide emulsion, which comprises the step of precipitating the silver halide in an aqueous hydrophilic colloid medium in the presence of a compound corresponding to the following general formula: Z-A-X, wherein: each of Z and X (the same or different) stands for a heterocycle or a heterocycle with fused-on ring, said heterocycle comprising the moiety =N—, and A stands for a chemical bond, alkylene, alkylene interrupted by oxygen or —N(R)— wherein R=hydrogen or alkyl comprising at most 4 C-atoms, arylene, alkenylene, —S-alkylene-S— or —S-alkylene, the alkylene groups of which can be interrupted by oxygen or —N(R)— wherein R has the same significance as above; said compound being present in an amount sufficient to restrain growth of silver halide grains. U.S. Pat. No. 3,704,130 discloses the following 2-alkylthio-benzimidazole-6-sulphonic acid compounds as Compound 7:

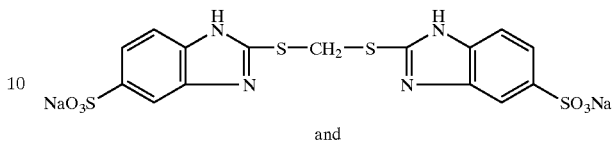

and

Compound 9:

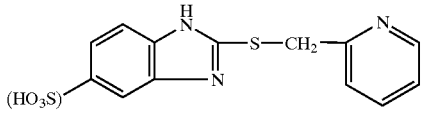

U.S. Pat. No. 4,639,408 discloses a process for forming an image comprising a heating step wherein a silver halide light-sensitive photographic material is heated in the presence of a compound represented by formula (I)

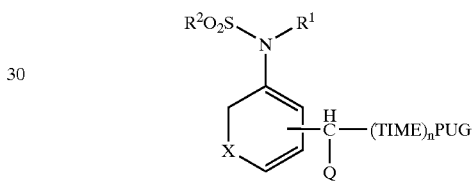

wherein X represents an atomic group completing a carbocyclic aromatic ring or a heterocyclic aromatic ring; $R^1$ is selected from selected from groups represented by formulae (A), (B), and (C):

| | |
|---|---|
| —SO$_2$—R$^{11}$ | (A) |
| —C(=O)—R$^{11}$ | (B) |
| —P(=O)R$^{11}$R$^{12}$ | (C) | in which $R^{11}$ and $R^{12}$ each represents a substituted or unsubstituted alkyl group, a cycloalkyl group, a substituted or unsubstituted aryl group, a substituted or unsubstituted heterocyclic group, an alkoxy or aryloxy group, an alkylthio or arylthio group, or a substituted or unsubstituted amino group, or $R^{11}$ and $R^{12}$ together form a 5-membered or 6-membered ring; $R^2$ represents a group selected from the groups represented by $R^{11}$; $R^1$ and $R^2$ together form a 5-membered or 6-membered ring; Q represents a hydrogen atom, an alkyl group, or an aryl group; TIME represents a timing group; PUG represents a photographically useful group; and n represents 0 or an integer, wherein the photographic material contains a base or a base precursor. U.S. Pat. No. 4,639,408 discloses the following 2-alkylthio-benzimidazole-6-sulphonic acid compounds as Compound (8):

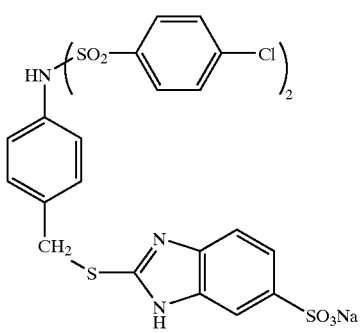

Compound (14):

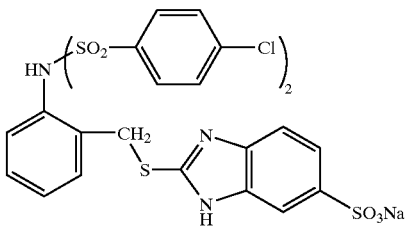

Compound (24):

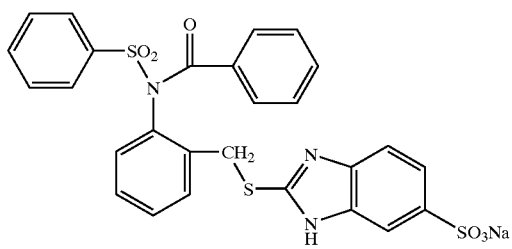

Compound (25):

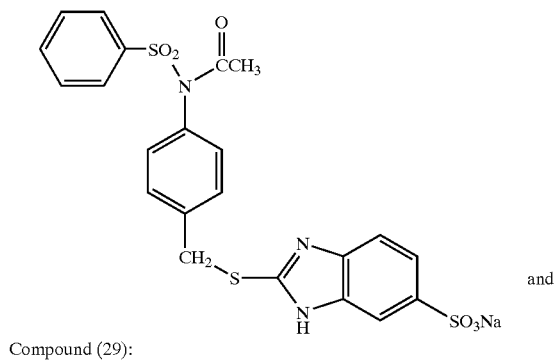

and

Compound (29):

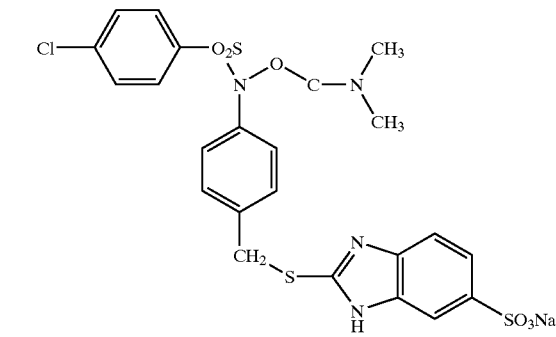

Surfactants with excellent latex-stabilizing properties, which enhance the adhesion of hydrophilic layers to hydrophobic supports, such as polyethylene terephthalate and hydrophobic thermosensitive elements of substantially light-insensitive thermographic recording materials, which are photographically inactive, which do not contain photographically inactive impurities and which is compatible with image-wise heating with a thermal head when incorporated into the outermost layer of substantially light-insensitive thermographic recording materials.

ULTRAVON™ W, an anionic alkyl-, benzyl-benzimidazole-sulfonic acid surfactant produced by Ciba, fulfils these requirements, except that being a mixture of at least 25 components it has variable properties and also often contains photographically active impurities, which have to be removed or rendered non-photographically active prior to use. Furthermore, it is no longer available.

ASPECTS OF THE INVENTION

It is therefore an aspect of the present invention to provide a surfactant with excellent latex-stabilizing properties.

It is therefore a further aspect of the present invention to provide a photographically inactive surfactant.

It is therefore also an aspect of the present invention to provide a photographically inactive surfactant without photographically active impurities.

It is therefore also an aspect of the present invention to provide a surfactant, which enhances the adhesion of hydrophilic layers to hydrophobic supports.

It is therefore also an aspect of the present invention to provide a surfactant, which is compatible with image-wise heating with a thermal head when incorporated into the outermost layer of substantially light-insensitive thermographic recording materials.

Further aspects and advantages of the invention will become apparent from the description hereinafter.

SUMMARY OF THE INVENTION

It has been surprisingly found that a compound represented by formula (I):

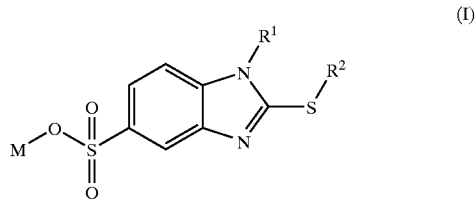

(I)

a compound represented by formula (II):

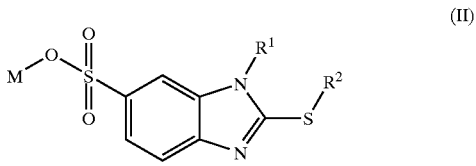

(II)

or a mixture of at least one compound represented by formula (I) and at least one compound represented by formula (II), wherein M is hydrogen, an alkali atom or an ammonium group; $R^1$ is hydrogen, a $-(CH_2)_mSO_3M$ group or a

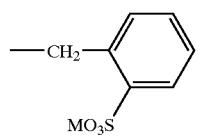

group; $R^2$ is an alkyl-, alkenyl- or alkynyl-group having 6 to 25 carbon atoms; and m is an integer between 1 and 5; exhibits excellent latex-stabilizing properties, enhances the adhesion of hydrophilic layers to hydrophobic supports, such as polyethylene terephthalate and hydrophobic thermosensitive elements of substantially light-insensitive thermographic recording materials, is photographically inactive and does not contain photographically inactive impurities. Furthermore, outermost layers of substantially light-insensitive thermographic recording materials containing compounds represented by formula (I), compounds represented by formula (II) or mixtures of at least one compound represented by formula (I) with at least one compound represented by formula (II) in which n is 12 to 24 surprisingly exhibit compatibility regarding transport properties with image-wise heating with a thermal head.

Aspects of the present invention are realized by a compound represented by formula (I):

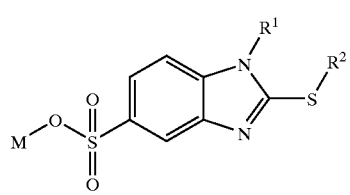

(I)

a compound represented by formula (II):

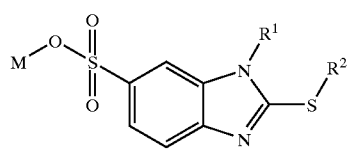

(II)

or a mixture of at least one compound represented by formula (I) with at least one compound represented by formula (II), wherein M is hydrogen, an alkali atom or an ammonium group; $R^1$ is hydrogen, a —$(CH_2)_m SO_3 M$ group or a

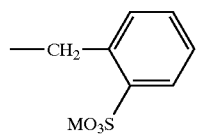

group; $R^2$ is an alkyl-, alkenyl- or alkynyl-group having 6 to 25 carbon atoms; and m is an integer between 1 and 5.

Aspects of the present invention are also realized by the use of at least one compound represented by the above-mentioned formula (I) at least one compound represented by the above-mentioned formula (II) or a mixture of at least one compound represented by the above-mentioned formula (I) and at least one compound represented by the above-mentioned formula (II) as a surfactant.

Aspects of the present invention are also realized by a photographic material comprising a support and at least one layer containing photosensitive silver halide, characterized in that said photographic material contains at least one compound represented by the above-mentioned formula (I), at least one compound represented by the above-mentioned formula (II) or a mixture of at least one compound represented by the above-mentioned formula (I) and at least one compound represented by the above-mentioned formula (II).

Preferred embodiments of the present invention are disclosed in the detailed description of the invention.

DETAILED DESCRIPTION OF THE INVENTION

Definitions

The terms alkyl, alkenyl and alkynyl mean an aliphatic hydrocarbon group and all variants possible for each number of carbon atoms in the group i.e. the group can be a straight chain or a branched group. For example for a three carbon atom alkyl group: n-propyl and isopropyl; for a four carbon atom alkyl group: n-butyl, isobutyl and tertiary-butyl; for a five carbon atom alkyl group: n-pentyl, 1,1-dimethyl-propyl, 2,2-dimethylpropyl and 2-methyl-butyl. Branched alkyl groups with Guerbet groups are particularly suitable e.g. —$CH_2$—$CH[$—$(CH_2)_9$—$CH_3]$—$(CH_2)_{11}$—$CH_3$, —$CH_2$—$CH[$—$(CH_2)_8$—$CH_3]$—$(CH_2)_{10}$—$CH_3$, —$CH_2$—$CH[$—$(CH_2)_7$—$CH_3]$—$(CH_2)_9$—$CH_3$, —$CH_2$—$CH[$—$(CH_2)_6$—$CH_3]$—$(CH_2)_8$—$CH_3$, —$CH_2$—$CH[$—$(CH_2)_5$—$CH_3]$—$(CH_2)_7$—$CH_3$, —$CH_2$—$CH[$—$(CH_2)_4$—$CH_3]$—$(CH_2)_6$—$CH_3$ and —$CH_2$—$CH[$—$(CH_2)_3$—$CH_3]$—$(CH_2)_5$—$CH_3$.

The terms thioalkyl-, thioalkenyl- and thioalkynyl-group mean a group consisting of a sulphur atom bonded to an alkyl-, alkenyl- or alkynyl-group, which is bonded via the sulphur atom to the entity to which the group is bonded.

The term sulphoalkyl group means an alkyl group substituted with a sulphonic acid group.

The term "tautomeric with" means that the two compounds interchange rapidly with one another in a liquid or dissolved state.

2-thioalkyl-benzimidazole-sulphonic Acid Compounds

According to a first embodiment of the compound, according to the present invention, $R^1$ is a —$(CH_2)_m SO_3 M$ group and $R^2$ is an alkyl, alkenyl or alkynyl group having 12 to 16 carbon atoms.

According to a second embodiment of the compound, according to the present invention, $R^1$ is a —$(CH_2)_4 SO_3 M$ group and $R^2$ is an alkyl, alkenyl or alkynyl group having 12 to 16 carbon atoms.

According to a third embodiment of the compound, according to the present invention, $R^1$ is a —$(CH_2)_4 SO_3 M$ group and n is and $R^2$ is an alkyl, alkenyl or alkynyl group having 12 to 24 carbon atoms.

Suitable 2-thioalkyl-benzimidazole-sulphonic acid compounds, according to the present invention, are:

| Compound nr | | |
|---|---|---|
| 01 | 2-thiododecyl-benzimidazole-5-sulphonic acid (tautomeric with 03) | 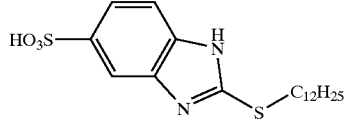 |
| 02 | 2-thiododecyl-benzimidazole-5-sulphonic acid sodium salt (tautomeric with 04) | |
| 03 | 2-thiododecyl-benzimidazole-6-sulphonic acid (tautomeric with 01) | |
| 04 | 2-thiododecyl-benzimidazole-6-sulphonic acid sodium salt (tautomeric with 02) | |
| 05 | 2-thiopentadecyl-benzimidazole-5-sulphonic acid (tautomeric with 07) | |
| 06 | 2-thiopentadecyl-benzimidazole-5-sulphonic acid sodium salt (tautomeric with 08) | |
| 07 | 2-thiopentadecyl-benzimidazole-6-sulphonic acid (tautomeric with 05) | |
| 08 | 2-thiopentadecyl-benzimidazole-6-sulphonic acid sodium salt (tautomeric with 06) | |
| 09 | 2-thiohexadecyl-benzimidazole-5-sulphonic acid (tautomeric with 11) | |
| 10 | 2-thiohexadecyl-benzimidazole-5-sulphonic acid sodium salt (tautomeric 12) | |
| 11 | 2-thiohexadecyl-benzimidazole-6-sulphonic acid (tautomeric with 09) | |
| 12 | 2-thiohexadecyl-benzimidazole-6-sulphonic acid sodium salt (tautomeric with 10) | |
| 13 | 2-thioheptadecyl-benzimidazole-5-sulphonic acid (tautomeric with 15) | |
| 14 | 2-thioheptadecyl-benzimidazole-5-sulphonic acid sodium salt (tautomeric with 16) | |
| 15 | 2-thioheptadecyl-benzimidazole-6-sulphonic acid (tautomeric with 13) | |
| 16 | 2-thioheptadecyl-benzimidazole-6-sulphonic acid sodium salt (tautomeric with 14) | |
| 17 | 2-thiododecyl,3-sulphopentyl-benzimidazole-5-sulphonic acid | |
| 18 | 2-thiododecyl,3-sulphopentyl-benzimidazole-5-sulphonic acid sodium salt | |
| 19 | 2-thiododecyl,3-sulphopentyl-benzimidazole-6-sulphonic acid | |
| 20 | 2-thiododecyl,3-sulphopentyl-benzimidazole-6-sulphonic acid sodium salt | |
| 21 | 2-thiopentadecyl,3-sulphopentyl-benzimidazole-5-sulphonic acid | |
| 22 | 2-thiopentadecyl,3-sulphopentyl-benzimidazole-5-sulphonic acid potassium salt | |
| 23 | 2-thiopentadecyl,3-sulphopentyl-benzimidazole-6-sulphonic acid | |
| 24 | 2-thiopentadecyl,3-sulphopentyl-benzimidazole-6-sulphonic acid potassium salt | |
| 25 | 2-thiohexadecyl,3-sulphopentyl-benzimidazole-5-sulphonic acid | |
| 26 | 2-thiohexadecyl,3-sulphopentyl-benzimidazole-5-sulphonic acid potassium salt | |
| 27 | 2-thiohexadecyl,3-sulphopentyl-benzimidazole-6-sulphonic acid | |
| 28 | 2-thiohexadecyl,3-sulphopentyl-benzimidazole-6-sulphonic acid potassium salt | |
| 29 | 2-thioheptadecyl,3-sulphopentyl-benzimidazole-5-sulphonic acid | |

-continued

| Compound nr | |
|---|---|
| 30 | 2-thioheptadecyl,3-sulphopentyl-benzimidazole-5-sulphonic acid potassium salt |
| 31 | 2-thioheptadecyl,3-sulphopentyl-benzimidazole-6-sulphonic acid |
| 32 | 2-thioheptadecyl,3-sulphopentyl-benzimidazole-6-sulphonic acid potassium salt |
| 33 | 2-thiododecyl,3-sulphobutyl-benzimidazole-5-sulphonic acid |
| 34 | 2-thiododecyl,3-sulphobutyl-benzimidazole-5-sulphonic acid potassium salt |
| 35 | 2-thiododecyl,3-sulphobutyl-benzimidazole-6-sulphonic acid |
| 36 | 2-thiododecyl,3-sulphobutyl-benzimidazole-6-sulphonic acid sodium salt 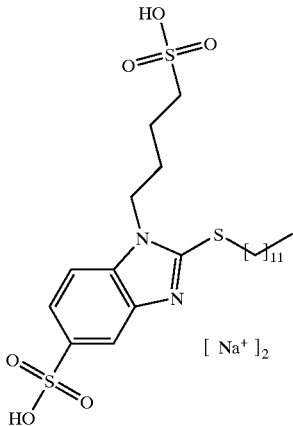 |
| 37 | 2-thiododecyl,3-sulphobutyl-benzimidazole-6-sulphonic acid potassium salt |
| 38 | 2-thiopentadecyl,3-sulphobutyl-benzimidazole-5-sulphonic acid |
| 39 | 2-thiopentadecyl 3-sulphobutyl-benzimidazole-5-sulphonic acid potassium salt |
| 40 | 2-thiopentadecyl,3-sulphobutyl-benzimidazole-6-sulphonic acid |
| 41 | 2-thiopentadecyl,3-sulphobutyl-benzimidazole-6-sulphonic acid potassium salt |
| 42 | 2-thiohexadecyl,3-sulpho-butyl-benzimidazole-5-sulphonic acid |
| 43 | 2-thiohexadecyl,3-sulphobutyl-benzimidazole-5-sulphonic acid sodium salt |
| 44 | 2-thiohexadecyl,3-sulpho-butyl-benzimidazole-5-sulphonic acid potassium salt |
| 45 | 2-thiohexadecyl,3-sulphobutyl-benzimidazole-6-sulphonic acid |

-continued

| Compound nr | | |
|---|---|---|
| 46 | 2-thiohexadecyl,3-sulphobutyl-benzimidazole-6-sulphonic acid sodium salt | 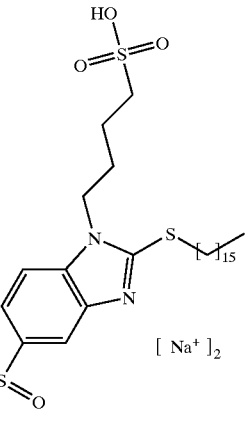 |
| 47 | 2-thiohexadecyl,3-sulphobutyl-benzimidazole-6-sulphonic acid potassium salt | |
| 48 | 2-thioheptadecyl,3-sulphobutyl-benzimidazole-5-sulphonic acid | |
| 49 | 2-thioheptadecyl,3-sulphobutyl-benzimidazole-5-sulphonic acid sodium salt | |
| 50 | 2-thioheptadecyl,3-sulphobutyl-benzimidazole-5-sulphonic acid potassium salt | |
| 51 | 2-thioheptadecyl,3-sulphobutyl-benzimidazole-6-sulphonic acid | |
| 52 | 2-thioheptadecyl,3-sulphobutyl-benzimidazole-6-sulphonic acid potassium salt | |
| 53 | 2-thiododecyl,3-sulphopropyl-benzimidazole-5-sulphonic acid | |
| 54 | 2-thiododecyl,3-sulphopropyl-benzimidazole-5-sulphonic acid sodium salt | |
| 55 | 2-thiododecyl,3-sulphopropyl-benzimidazole-5-sulphonic acid potassium salt | |
| 56 | 2-thiododecyl,3-sulphopropyl-benzimidazole-6-sulphonic acid | |
| 57 | 2-thiododecyl,3-sulphopropyl-benzimidazole-6-sulphonic acid potassium salt | |
| 58 | 2-thiododecyl,3-sulphopropyl-benzimidazole-6-sulphonic acid sodium salt | |
| 59 | 2-thiopentadecyl,3-sulphopropyl-benzimidazole-5-sulphonic acid | |
| 60 | 2-thiopentadecyl,3-sulphopropyl-benzimidazole-5-sulphonic acid potassium salt | |
| 61 | 2-thiopentadecyl,3-sulphopropyl-benzimidazole-6-sulphonic acid | |
| 62 | 2-thiopentadecyl,3-sulphopropyl-benzimidazole-6-sulphonic acid potassium salt | |
| 63 | 2-thiohexadecyl,3-sulphopropyl-benzimidazole-5-sulphonic-acid | |
| 64 | 2-thiohexadecyl,3-sulphopropyl-benzimidazole-5-sulphonic acid potassium salt | |
| 65 | 2-thiohexadecyl,3-sulphopropyl-benzimidazole-5-sulphonic acid sodium salt | |
| 66 | 2-thiohexadecyl,3-sulphopropyl-benzimidazole-6-sulphonic acid | |
| 67 | 2-thiohexadecyl,3-sulphopropyl-benzimidazole-6-sulphonic acid potassium salt | |

-continued

| Compound nr | |
|---|---|
| 68 | 2-thioheptadecyl,3-sulphopropyl-benzimidazole-5-sulphonic acid |
| 69 | 2-thioheptadecyl,3-sulphopropyl-benzimidazole-5-sulphonic acid potassium salt |
| 70 | 2-thioheptadecyl,3-sulphopropyl-benzimidazole-6-sulphonic acid |
| 71 | 2-thioheptadecyl,3-sulphopropyl-benzimidazole-6-sulphonic acid potassium salt |
| 72 | 2-thiododecyl,3-sulphoethyl-benzimidazole-5-sulphonic acid |
| 73 | 2-thiododecyl,3-sulphoethyl-benzimidazole-5-sulphonic acid potassium salt |
| 74 | 2-thiododecyl,3-sulphoethyl-benzimidazole-6-sulphonic acid |
| 75 | 2-thiododecyl,3-sulphoethyl-benzimidazole-6-sulphonic acid potassium salt |
| 76 | 2-thiopentadecyl,3-sulphoethyl-benzimidazole-5-sulphonic acid |
| 77 | 2-thiopentadecyl,3-sulphoethyl-benzimidazole-5-sulphonic acid potassium salt |
| 78 | 2-thiopentadecyl,3-sulphoethyl-benzimidazole-6-sulphonic acid |
| 79 | 2-thiopentadecyl,3-sulphoethyl-benzimidazole-6-sulphonic acid potassium salt |
| 80 | 2-thiohexadecyl,3-sulpho-ethyl-benzimidazole-5-sulphonic acid |
| 81 | 2-thiohexadecyl,3-sulphoethyl-benzimidazole-6-sulphonic acid |
| 82 | 2-thiohexadecyl,3-sulphoethyl-benzimidazole-6-sulphonic acid potassium salt |
| 83 | 2-thioheptadecyl,3-sulphoethyl-benzimidazole-5-sulphonic acid |
| 84 | 2-thioheptadecyl,3-sulphoethyl-benzimidazole-5-sulphonic acid potassium salt |
| 85 | 2-thioheptadecyl,3-sulphoethyl-benzimidazole-6-sulphonic acid |
| 86 | 2-thioheptadecyl,3-sulphoethyl-benzimidazole-6-sulphonic acid potassium salt |

—(CH$_2$)$_m$SO$_3$M group and

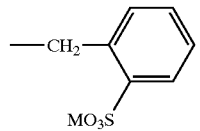

groups can be incorporated into 2-alkyl- or 2-thioalkyl-benzimidazole-sulphonic acids by reaction with alkanesultones, such as 1,4-butanesultone and 1,3-propanesultone, and 3H-2,1-benzothiazole,1,1-dioxide (α-hydroxy-o-toluenesulfonic acid-γ-sultone or o-tolyl sultone) respectively.

Photographic Material

The photographic material may be developable with a conventional photographic developer or may be thermally developable i.e. the photographic material is a photothermographic material.

Photothermographic Material

According to a first embodiment of the photographic material, according to the present invention, the photothermographic material is a photothermographic material in which the layer containing photosensitive halide is at least part of a photo-addressable thermally developable element, said thermally developable element further comprising a substantially light-insensitive organic silver salt, a reducing agent therefor in thermal working relationship therewith and a binder.

If the photographic material is a photothermographic material containing a substantially light-insensitive organic silver salt, for example a substantially light-insensitive silver salt of an organic carboxylic acid, the photosensitive silver halide present may be employed in a range of 0.1 to 100 mol percent; preferably, from 0.2 to 80 mol percent; particularly preferably from 0.3 to 50 mol percent; especially preferably from 0.5 to 35 mol %; and especially from 1 to 12 mol % of substantially light-insensitive organic silver salt. Furthermore, in such a material so-called in-situ silver halide can be prepared by conversion of a substantially light-insensitive silver salt of an organic carboxylic acid with a non-fluoro halide ion source such as described in U.S. Pat. No. 3,457,075, WO 97/48104 and WO 97/48105.

Photosensitive Silver Halide

The photosensitive silver halide used the present invention may be any photosensitive silver halide such as silver bromide, silver iodide, silver chloride, silver bromoiodide, silver chlorobromoiodide, silver chlorobromide etc. The silver halide may be in any form which is photosensitive including, but not limited to, cubic, orthorhombic, tabular, tetrahedral, octagonal etc. and may have epitaxial growth of crystals thereon.

According to a second embodiment of the photographic material, according to the present invention, the layer containing silver halide is a silver halide emulsion layer.

According to a third embodiment of the photographic material, according to the present invention, the layer containing silver halide is a silver halide emulsion layer comprising cubic silver bromide or silver bromoiodide crystals with an amount of at most 3 mole % of iodide.

According to a fourth embodiment of the photographic material, according to the present invention, the layer containing silver halide is a silver halide emulsion layer comprising monodisperse silver bromide or silver bromoiodide crystals. A monodisperse size distribution is obtained when 95% of the grains have a size that does not deviate more than 30% from the average grain size.

Cubic crystals are especially preferred as they allow rapid processing. In principle the same is possible with flat tabular crystals but, due to their heterogeneous silver halide grain distribution, their gradation is too low and due to the light-reflection of the developed silver which is situated at longer wavelengths the image tone is not neutral, but shifted to a reddish brown colour.

The silver bromide or silver bromoiodide emulsions used in accordance with this invention may be prepared by mixing the halide and silver salt solutions in partially or fully controlled conditions of temperature, concentrations, sequence of addition, and rates of addition. The silver halide is preferably precipitated according to the double-jet method, in the presence of a colloid binder in a temperature-controlled vessel provided with absolution inlet and stirring unit.

A preferred precipitation technique is the double-jet method, wherein the silver ion concentration is controlled during the precipitation and wherein the flow rate of the reacting solutions is enhanced as the precipitation proceeds, at such a rate that no renucleation appears. This method offers the possibility of obtaining well-defined crystals having a regular cubic habit within a short precipitation time. Preferred cubic silver bromide or silver bromoioidide crystals have a crystal size between 0.1 and 0.4 $\mu$m and even more preferably between 0.30 and 0.35 $\mu$m for reasons of image tone of the developed silver halide crystals. As a result a high covering power of the developed grains is obtained.

The silver halide used in the present invention may be employed without modification in the case of use in photothermographic materials, but for photographic emulsion materials and optionally in photothermographic material, however, it may be chemically sensitized with a chemical sensitizing agent such as a compound containing sulphur, selenium, tellurium etc., or a compound containing gold, platinum, palladium, iron, ruthenium, rhodium or iridium etc., a reducing agent such as a tin halide etc., or a combination thereof.

Details of these procedures are described in T. H. James, "The Theory of the Photographic Process", Fourth Edition, Macmillan Publishing Co. Inc., New York (1977), Chapter 5, pages 149 to 169, in "Chimie et Physique Photographique" by P. Glafkides, in "Photographic Emulsion Chemistry" by G. F. Duffin, in "Making and Coating Photographic Emulsion" by V. L. Zelikman et al, and in "Die Grundlagen der Photographischen Prozesse mit Silberhalogeniden" edited by H. Frieser and published by Akademische Verlagsgesellschaft (1968). As described in this literature chemical sensitization may be carried out by effecting the ripening in the presence of small amounts of compounds containing sulphur e.g. thiosulphate, thiocyanate, thioureas, sulphites, mercapto compounds, and rhodamines. The emulsions may also be sensitized by gold-sulphur ripeners or by means of reducing agents e.g. tin compounds as described in GB-A 789,823, amines, hydrazine derivatives, formamidine-sulphinic acids, and silane compounds. Chemical sensitization may also be performed with small amounts of Ir, Rh, Ru, Pb, Cd, Hg, Tl, Pd, Pt, or Au. One of these chemical sensitization methods or a combination thereof may be used.

Preferably the silver halide crystals are predigested with weakly oxidizing compounds as e.g. thiosulphonic acids before being chemically ripened. Chemical sensitization may occur in the presence of spectral sensitizers.

The grain size of the silver halide particles can be determined by the Moeller Teller method in the sample containing silver halide particles is sedimented upon a filter paper, which is submerged in electrolyte together with a negative platinum needle-shaped electrode and a reference electrode. The silver halide particles on the filter paper are slowly scanned individually with the needle-shaped electrode, whereupon the silver halide grains are individually electrochemically reduced at the cathode. This electrochemical reduction is accompanied by a current pulse, which is registered as a function of time and integrated to give the charge transfer Q for the electrochemical reduction of the silver halide particle, which is proportional to its volume. From their volume the equivalent circular grain diameter of each grain can be determined and therefrom the average particle size and size distribution.

Binders

Colloidal binders used during the silver halide precipitation in the preparation of silver halide emulsion are hydrophilic binders such as the frequently used gelatin. Gelatin may, however, be replaced in part or integrally by synthetic, semi-synthetic, or natural polymers. Synthetic substitutes for gelatin are e.g. polyvinyl alcohol, poly-N-vinyl pyrrolidone, polyvinyl imidazole, polyvinyl pyrazole, polyacrylamide, polyacrylic acid, and derivatives thereof, in particular copolymers thereof. Natural substitutes for gelatin are e.g. other proteins such as zein, albumin and casein, cellulose, saccharides, starch, and alginates. In general, the semi-synthetic substitutes for gelatin are modified natural products e.g. gelatin derivatives obtained by conversion of gelatin with alkylating or acylating agents, by grafting of polymerizable monomers on gelatin or prehardened gelatins with blocked functional groups as a consequence of this prehardening treatment, and cellulose derivatives such as hydroxyalkyl cellulose, carboxymethyl cellulose, phthaloyl cellulose, and cellulose sulphates.

The binder should of course dispose of an acceptably high number of functional groups, which by reaction with an appropriate hardening agent can provide a sufficiently resistant layer. Such functional groups are especially the amino groups, but also carboxylic groups, hydroxy groups, and active methylene groups.

Another substitute for gelatin may be silica.

If gelatin is used as a binder gelatin may be lime-treated or acid-treated. The preparation of such gelatin types has been described in e.g. "The Science and Technology of Gelatin", edited by A. G. Ward and A. Courts, Academic Press 1977, page 295 and next pages. The gelatin may also be an enzyme-treated gelatin as described in Bull. Soc. Sci. Phot. Japan, No. 16, page 30 (1966). Preferably, use is made of photographically inert gelatin so as to add a reproducible amount of chemical sensitizers at the end of the precipitation or after flocculation or washing or redispersing the silver halide emulsion. To get a qualitatively good flocculate flocculating agents as e.g. polystyrene sulphonic acid etc. may be added before or after acidifying the emulsion. Other possibilities are offered by filtration techniques e.g. dialysis, ultrafiltration etc. so that the emulsion may be washed to a desired pAg value without the requirement to be redispersed afterwards. Emulsion flocculates need to be washed out by the addition of well-determined amounts of demineralized water, whether or not doped with small amounts of water-soluble salts.

Spectral Sensitizers

According to a fifth embodiment of the photographic material, according to the present invention, the layer containing silver halide further contains a spectral sensitizer. The spectral sensitizer are chosen as a function of the light source, showing a high light absorption at the exposure wavelength of the light source.

Spectral sensitizers may be added partially before, partially after or integrally after chemical sensitization with a total amount needed to reach the optimal coverage degree.

The light-sensitive silver halide emulsions may be spectrally sensitized with methine dyes such as those described by F. M. Hamer in "The Cyanine Dyes and Related Compounds", 1964, John Wiley & Sons. Dyes that may be used for the purpose of spectral sensitization include cyanine dyes, merocyanine dyes, complex cyanine dyes, complex merocyanine dyes, holopolar cyanine dyes, hemicyanine dyes, styryl dyes and hemioxonol dyes. Particularly valuable dyes are those belonging to the cyanine dyes, merocyanine dyes, complex merocyanine dyes, rhodacyanine dyes.

Preferred rhodacyanine dyes for use in the photographic materials, according to the present invention, have chemical structures as described in EP-A 473 209.

Other dyes, which do not have any spectral sensitization activity, or certain other compounds, which do not substantially absorb visible radiation, may have a supersensitization effect when they are incorporated together with said spectral sensitizing agents into the emulsion. Suitable supersensitizers include heterocyclic mercapto compounds containing at least one electronegative substituent as described e.g. in U.S. Pat. No. 3,457,078, nitrogen-containing heterocyclic ring-substituted amino-stilbene compounds as described e.g. in U.S. Pat. No. 2,933,390 and U.S. Pat. No. 3,635,721, aromatic organic acid/formaldehyde condensation products as described e.g. in U.S. Pat. No. 3,743,510, cadmium salts, and azaindene compounds.

Stabilizers

According to a sixth embodiment of the photographic material, according to the present invention, the layer containing silver halide further contains at least one compound for preventing the formation of fog or stabilizing the photographic characteristics during the production or storage of photographic elements or during the photographic treatment thereof. Many known compounds may be added as fog-inhibiting agent or stabilizer to the silver halide emulsion. Suitable examples are i.a. the heterocyclic nitrogen-containing compounds such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles (preferably 5-methyl-benzotriazole), nitrobenzotriazoles, mercaptotetrazoles, in particular 1-phenyl-5-mercaptotetrazole, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2–58, triazolopyrimidines such as those described in GB-A 1,203,757, GB-A 1,209,146, JN 75-39537, and GB-A 1,500,278, and 7-hydroxy-s-triazolo-[1,5-a]-pyrimidines as described in U.S. Pat. No. 4,727,017, and other compounds such as benzene-thiosulphonic acid, benzenethiosulphinic acid, benzenethiosulphonic acid amide. Other compounds that may be used as fog-inhibiting compounds are metal, salts such as e.g. mercury or cadmium salts and the compounds described in Research Disclosure No 17643 (1978), Chaptre VI.

Preferred stabilizers added to the emulsion in accordance with this invention are e.g. 4-hydroxy-6-methyl-1,3,3a,7-tetraazaindene and 1-phenyl-5-mercaptotetrazole, thioether substituted 1-phenyl-5-mercaptotetrazoles as described in EP-A 53 851 being more preferable, especially if they have a solubilizable group as those described in Research Disclosure No. 24236 (1984).

The fog-inhibiting agents or stabilizers can be added to the silver halide emulsion prior to, during, or after the ripening thereof and mixtures of two or more of these compounds may be used.

Support

According to a second embodiment of the photographic material, according to the present invention, the support is transparent or translucent. Thin flexible supports of transparent resin film are preferred, e.g. of a cellulose ester, e.g. cellulose triacetate, polypropylene, polycarbonate or polyester, e.g. poly(ethylene terephthalate). The support may be in sheet, ribbon or web form and subbed if need be to improve the adherence to the thereon coated thermosensitive element. The support may be dyed or pigmented to provide a transparent coloured background for the image.

Subbing Layers and Subbing Layer Systems

According to a third embodiment of the photographic material, according to the present invention, said support is provided with at least one subbing layer or subbing layer system.

According to a fourth embodiment of the photographic material, according to the present invention, said support is provided with at least one subbing layer or subbing layer system and at least one subbing layer or subbing layer system contains at least one compound represented by said formula (I), at least one compound represented by said formula (II) or a mixture of at least one compound represented by said formula (I) and at least one compound represented by said formula (II).

The term subbing layer system refers to more than one layer fulfilling the function of subbing, subbing meaning provision of a means of providing adhesion of a functional layer to a support. For example, in photothermographic materials a combination of two layers is often used to provide adhesion of a photographic silver halide and gelatin-containing emulsion layer to a poly(ethylene terephthalate)

support, the layer adjacent to the poly(ethylene terephthalate) support often comprising a polymer latex, e.g. a terpolymer latex of vinylidene chloride/methyl acrylate/ itaconic acid (88/10/2 by weight), colloidal silica and anionic surfactants, and the second layer in the subbing layer system often comprising gelatin, colloidal silica and anionic surfactants.

It is preferred that at least one compound represented by said formula (I), at least one compound represented by said formula (II) or a mixture of at least one compound represented by said formula (I) and at least one compound represented by said formula (II) be present in at least one and preferably all the layers of a subbing layer system used in photographic materials. This is not only because of the photographically inert nature of compounds represented by formula's (I) and (II) and the absence of photographically active impurities, but also because of the improved wettability of subbing layers and of the outermost layer of subbing layer systems resulting in improved overcoatability and faster coating compared with alternative surfactants such as ULTRAVON™ W from Ciba-Geigy.

Preferred additional ingredients for the subbing layer used in accordance with the present invention are a polymer latex and polyethylene wax. Particularly preferred polymer latexes for use in the subbing layer of the present invention are producible with monomers selected from the group consisting of acrylates, methacrylates, vinyl esters, acrylic acid, methacrylic acid, itaconic acid, vinylidene chloride, polyisocyanates, aromatic polycarboxylic acids and polyols.

Suitable additional ingredients for use in the subbing layer of the photographic material, according to the present invention, are:

sorbitol;

a terpolymer latex of vinylidene chloride/methyl acrylate/ itaconic acid (88/10/2 by weight);

gelatin e.g. K 18435, a calcium-free medium viscosity gelatin from DGF STOESS;

microcrystalline polyethylene wax e.g. MOBILCER™ Q from Mobil Oil;

polymethylmethacrylate particles;

silica e.g. KIESELSOL 100F and KIESELSOL 300F, 30% by weight aqueous dispersions of colloidal silica from BAYER, and, a 30% aqueous dispersion of colloidal silica from BAYER; and additional non-ionic and anionic surfactants.

It is particularly preferred to post-stabilize latexes such a terpolymer latex of vinylidene chloride/methylacrylate/ itaconic acid (88/10/2 by weight) with at least one compound represented by said formula (I), at least one compound represented by said formula (II) or a mixture of at least one compound represented by said formula (I) and at least one compound represented by said formula (II) e.g. a mixture of Compounds 75 and 78.

Coating Techniques

The coating of any layer of the substantially light-insensitive thermographic recording material used in the present invention may proceed by any coating technique e.g. such as described in Modern Coating and Drying Technology, edited by Edward D. Cohen and Edgar B. Gutoff, (1992) VCH Publishers Inc., 220 East 23$^{rd}$ Street, Suite 909 New York, N.Y. 10010, USA. Coating may proceed from aqueous or solvent media with overcoating of dried, partially dried or undried layers.

Industrial Application

The compounds according to the present invention are used as surfactants in the subbing layers and subbing layer configurations of photographic materials, in the subbing layers, subbing layer configurations and protective layers of substantially light-insensitive thermographic recording materials and in the post-stabilization of polymer latexes.

The invention is illustrated hereinafter by way of comparative examples and invention examples. The percentages and ratios given in these examples are by weight unless otherwise indicated.

Synthesis of Compounds Represented by Formula's (I) and (II)

General Synthesis Route for Compounds 2, 4, 10, 14 etc.:

The sodium salt of 2-mercapto-benzimidazole-5-sulphonic acid was S-alkylated in the presence of DIPEA (N,N-diisopropylethylamine) as base in dimethyl acetamide by reaction with the corresponding alkyl bromide by stirring overnight at 52° C. In this way alkylation could be carried out selectively at the mercapto-group and could be suppressed at the 1-position. A yield of up to 96% of compound 10 was obtained in the case of cetyl bromide.

Synthesis of Compound 10:

1728 g of the monosodium salt of 2-mercapto-benzimidazole-5-sulphonic acid and 3150 mL of dimethyl acetamide were added to a 10 liter vessel provided with a compressed air stirrer, a dropping funnel and a reflux condenser was placed in an oil bath. 1359 mL of DIPEA were then added to this heterogeneous mixture with stirring and the light-brown suspension heated to 40° C. 2382 g of cetyl bromide was added dropwise and the mixture heated to 52° C. There was no increase in temperature during this step. The reaction was carried out with stirring at 52° C. for 20 hours after which the reaction was virtually complete. The mixture was then transferred to a 20 liter vessel, cooled to room temperature and 6 L of acetone was added with stirring and the stirring continued for 1 hour after the addition was completed. A thick suspension was obtained, which is relatively difficult to stir. The product was then filtered off, twice washed with 800 mL of a 1:2 mixture of dimethyl acetamide/acetone, twice washed with 1400 mL of a 1:3 mixture of dimethyl acetamide/acetone, washed four times with 1200 mL of acetone and finally dried in a forced air drying cupboard at 45° C. for 2 days. 2.53 kg of Compound 10 (sodium salt of 2-thiohexadecyl-benzimidazole-5-sulphonic acid) was obtained corresponding to a yield of 89% and contained 4 mol % of dimethyl acetamide and 7 mol % of DIPEA.

Synthesis of a Mixture of the Structural Isomers Compound 43 and Compound 46:

1190 g of Compound 10 (sodium salt of 2-thiohexadecyl-benzimidazole-5-sulphonic acid) and 3890 mL of dimethyl acetamide were added to a 10 liter vessel provided with a compressed air stirrer, a dropping funnel and a reflux condenser was placed in an oil bath. 103.9 g of 97% sodium hydroxide were then added with stirring and the mixture heated to 80° C. The heat source was then removed and 252.4 mL of butanesultone added over a period of 5 minutes, whereupon the temperature increased to 94° C. After addition of a third of this quantity of butanesultone a white precipitate is formed and the mixture becomes more difficult to stir after addition was completed. The reaction mixture was then cooled to 50° C. and 5170 mL of acetone added with stirring. The product precipitates out and the suspension becomes more difficult to stir. The product was then: filtered off, washed with 2 L of a 1:3 mixture of dimethyl acetamide/acetone, stirred with 14 L of a 1:3 mixture of dimethyl acetamide/acetone, filtered again, twice washed with 4 L of a 1:3 mixture of dimethyl acetamide/acetone, washed 6 times with 2 L of acetone and then dried to constant weight in a forced air drying cupboard at 45° C. The product a mixture of the structural isomers: Compound 43 (2-thiohexadecyl,3-sulphobutyl-benzimidazole-5-sulphonic acid sodium salt) and Compound 46 (2-thiohexadecyl,3-sulphobutyl-benzimidazole-6-sulphonic acid sodium salt) was obtained in a yield of 95%.

Separation of Compound 43 (2-thiohexadecyl,3-sulphobutyl-benzimidazole-5-sulphonic acid sodium salt) and Compound 46 (2-thiohexadecyl,3-sulphobutyl-benzimidazole-6-sulphonic acid sodium salt) could be realized by working up the product before adding acetone to the reaction mixture. After filtration, washing and treatment with warm dimethyl acetamide almost pure Compound 43 (2-thiohexadecyl,3-sulphobutyl-benzimidazole-5-sulphonic acid sodium salt) was isolated. The second structural isomer, Compound 46 (2-thiohexadecyl,3-sulphobutyl-benzimidazole-6-sulphonic acid sodium salt) was extracted from the filtrate by adding acetone.

| Ingredients used in the EXAMPLES: | |
|---|---|
| ULTRAVON W = | a sodium arylsulfonate surfactant from Ciba-Geigy |
| ARKOPON T = | a 40% concentrate of a sodium salt of N-methyl-N-2-sulfoethyl-oleylamide from CLARIANT |
| ARKOPAL ™ N060 = | a nonylphenylpolyethylene-glycol from CLARIANT |
| NIAPROOF ANIONIC ™ 4 = | a 27% concentrate of a sodium 1-(2'-ethylbutyl)-4-ethylhexylsulphate from NIACET |
| FLUORAD ™ FX1005 = | ammonium salt of perfluoro-octanoic acid from 3M |
| SURF 09 = | a 1:1 mixture of Compound 75 and Compound 78 |
| K 18114 = | a gelatin from DGF STOESS | antihalo dye =

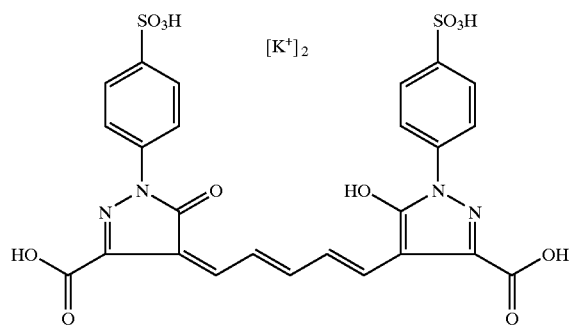

COMPARATIVE EXAMPLES 1 TO 3 AND INVENTION EXAMPLE 1

The post-stabilization of a 30% by weight terpolymer latex of vinylidene chloride/methyl acrylate/itaconic acid (88/10/2 by weight) was investigated in an accelerated stability test at 60° C. in a drying cupboard and an autocoagulation test at 80° C. in a drying cupboard with different surfactants (see above). The results of these tests are shown in Table 1:

SURF 09, a 1:1 mixture of Compound 75 and Compound 78 exhibited significantly better post-stabilization behaviour compared with other surfactants including ULTRAVON™ W.

TABLE 1

| | Anionic surfactant | | time after which settling first observed in stability test at 60° C. [h] | time to auto-coagulation in autocoagulation test at 80° C. [h] |
|---|---|---|---|---|
| | type | quantity in g/100 g latex | | |
| Comparative example nr | | | | |
| 1 | none | — | 14 | 8.5 |
| 2 | ARKOPON ™ T | 0.78 | 254 | 36.5 |
| 3 | ULTRAVON ™ W | 1.09 | 94 | 17.5 to 26.5 |
| Invention example nr | | | | |
| 1 | SURF 09 | 0.78 | >254 | >48 |

COMPARATIVE EXAMPLES 4 TO 6 AND INVENTION EXAMPLES 2 to 4

The subbed-supports used in the overcoatability experiments of COMPARATIVE EXAMPLES 4 to 6 and INVENTION EXAMPLES 2 to 4 were prepared by coating both sides of a 350 μm thick poly(ethylene terephthalate) sheet already stretched in the length direction as an aqueous dispersion which after drying and transverse stretching produced a 100 μm thick support coated with the following conductive layer composition expressed as the coating weights of the ingredients present, being the first layer in the subbing layer system:

| | |
|---|---|
| terpolymer latex of vinylidene chloride/methyl acrylate/itaconic acid (88/10/2): | 147 mg/m$^2$ |
| colloidal silica (KIESELSOL ™ 100F from BAYER): | 16 mg/m$^2$ |
| sorbitol | 25 mg/m$^2$ |
| MERSOLAT ™ H80, a sodium hexadecyl-sulfonate from BAYER | 0.7 mg/m$^2$ |

The second layer of the subbing layer system was then applied as an aqueous dispersion to both sides of the 100 μm thick poly(ethylene terephthalate) support, which after drying at 130° C. produced the following composition expressed as the coating weights of the ingredients present:

| | |
|---|---|
| gelatin (K 18435): | 190 mg/m$^2$ |
| colloidal silica (KIESELSON ™ 300F): | 170 mg/m$^2$ |
| 3.2 μm polymethyl methacrylate latex particles: | 1 mg/m$^2$ |
| 2-methyl-2,4-pentanediol: | 11 mg/m$^2$ |
| trimethylolpropane | 5.6 mg/m$^2$ |
| ARKOPAL ™ N060: | 3.3 mg/m$^2$ |
| an anionic surfactant | 6.7 mg/m$^2$ |

These two layers together form the subbing layer systems of COMPARATIVE EXAMPLE 4 and INVENTION EXAMPLE 2.

The overcoatability of these subbing layer systems was evaluated with an aqueous antihalation layer coating dispersion with the composition after drying of:

| | |
|---|---|
| gelatin (K 18814): | 3100 mg/m$^2$ |
| colloidal silica (KIESELSOL # 300F): | 590 mg/m$^2$ |
| terpolymer latex of methyl acrylate/acrylic acid/tetra-allyloxyethane (37/46.5/16.5): | 1400 mg/m$^2$ |
| antihalo dye (see above): | 100 mg/m$^2$ |
| MOBILCER ™ Q, a microcrystalline polyethylene wax from Mobil Oil: | 2.5 mg/m$^2$ |
| glyoxal (HCOHCO) as hardener: | 72 mg/m$^2$ |
| 7.5 μm polymethyl methacrylate latex particles: | 28 mg/m$^2$ |
| ARKOPON ™ T: | 6 mg/m$^2$ |
| NIAPROOF ANIONIC 4: | 1 mg/m$^2$ |
| FLUORAD ™ FX1005: | 1.5 mg/m$^2$ |

The results obtained with a slide hopper (cascade) coating machine are given in Table 2 below:

TABLE 2

| | Anionic surfactant in second layer of subbing layer system | Coating speed (m/min) | Minimum vacuum in machine to obtain coating [Pa] | Coating length in cm needed to remedy coating faults e.g. induced by tape splice |
|---|---|---|---|---|
| Comparative example nr | | | | |
| 4 | ULTRAVON ™ W | 180 | 50 | 42 |
| 5 | ULTRAVON ™ W | 220 | 80 | 9* |
| 6 | ULTRAVON ™ W | 250 | 360 | 225* |

TABLE 2-continued

|  | Anionic surfactant in second layer of subbing layer system | Coating speed (m/min) | Minimum vacuum in machine to obtain coating [Pa] | Coating length in cm needed to remedy coating faults e.g. induced by tape splice |
|---|---|---|---|---|
| Invention example nr |  |  |  |  |
| 2 | SURF 09 | 180 | 60 | 25 |
| 3 | SURF 09 | 220 | 50 | 9 |
| 4 | SURF 09 | 250 | 120 | 34 |

*coating fault not remedied at edge

It is clear from the results in Table 2, that the use of SURF 09 as an anionic surfactant in the second (outermost) layer of the subbing layer system instead of ULTRAVON™ W substantially improved the overcoatability of the subbing layer system with the antihalation layer coating dispersion, particularly at coating speeds of 220 to 250 m/minute where otherwise coating faults were not remedied at the edges of the coating.

COMPARATIVE EXAMPLES 7 AND 8 AND INVENTION EXAMPLE 5

The subbed-supports used in the photographic materials of COMPARATIVE EXAMPLES 7 and 8 and INVENTION EXAMPLE 5 were prepared as described for the overcoatability experiments of COMPARATIVE EXAMPLES 4 to 6 and INVENTION EXAMPLES 2 to 4 except that MERSO-LAT™ H80 in the first layer was replaced by ULTRAVON™ W or ARKOPON™ T or SURF 09. The surfactants used in the first and second layers of the subbing layer system used in the photographic materials of COMPARATIVE EXAMPLES 7 and 8 and INVENTION EXAMPLES are given in Table 3.

The photographic materials of COMPARATIVE EXAMPLES 7 and 8 and INVENTION EXAMPLE 5 were prepared by coating onto both sides of the above-described support the same silver halide emulsion as that used in the blue-sensitive universal X-ray film type CP-BU produced by AGFA-GEVAERT. The material before and after heating for 36 h at 57° C. at 34% relative humidity was exposed through a density wedge (continuously varying carbon-coated wedge (constant 0.15) by visible light a from projection lamp (130V; 250W—having an exposure voltage of 85V) during 0.1 s at a distance of 1.7 m from the film, a densitometric filter with a density of 0.30 and a "Corning filter 5850" as a blue filter with a density of 2.64 (measured with a Macbeth TR 924 densitometer). The light sensitivity, S, is the log of the light exposure in $\mu J/cm^2$ needed to obtain a density of 1.00 above fog density, which is lower for materials with a higher sensitivity to light, and the minimum density was determined from the wedge patterns obtained after development at 33° C. for 90 seconds in a G1381 M 6/5 developer produced by AGFA-GEVAERT. The sensitivities and minimum densities Dmin obtained for the photographic materials of COMPARATIVE EXAMPLES 7 and 8 and INVENTION EXAMPLE 5 before and after heating for 36 h at 57° C. at 34% relative humidity are summarized in Table 3.

TABLE 3

|  | Anionic surfactant in 1st layer of subbing layer system | | Anionic surfactant in 2nd layer of subbing layer system | | fresh material | | material after 36 h/ 57° C./34% RH | |
|---|---|---|---|---|---|---|---|---|
|  | type | quantity [mg/m²] | type | quantity [mg/m²] | Dmin | S | Dmin | S |
| Comparative example nr |  |  |  |  |  |  |  |  |
| 7 | ULTRAVON ™ W | 4.0 | ULTRAVON ™ W | 6.7 | 0.064 | 1.66 | 0.145 | 1.67 |
| 8 | ARKOPON ™ T | 5.0 | ARKOPON ™ T | 6.7 | 0.061 | 1.66 | 0.146 | 1.66 |
| Invention example nr |  |  |  |  |  |  |  |  |
| 5 | SURF 09 | 4.0 | SURF 09 | 6.7 | 0.058 | 1.66 | 0.124 | 1.65 |

From the results in Table 3, it is clear that after heating for 36 h at 57° C. at 34% relative humidity the photographic material of INVENTION EXAMPLE 5 with SURF 09 in both the first and outermost (second) layer of the subbing layer system resulted in a significantly lower increase in Dmin than the photographic materials of COMPARATIVE EXAMPLES 7 and 8 with ULTRAVON™ W and ARKOPON™ T respectively in both the first and outermost (second) layer of the subbing layer system, indicating the lower photographic activity of SURF 09 compared with ULTRAVON™ W and ARKOPON™ T.

The present invention may include any feature or combination of is features disclosed herein either implicitly or explicitly or any generalisation thereof irrespective of whether it relates to the presently claimed invention. In view of the foregoing description it will be evident to a person skilled in the art that various modifications may be made within the scope of the invention.

We claim:

1. A photographic material comprising a support and at least one layer containing photosensitive silver halide, characterized in that said photographic material contains at least one compound represented by formula (I):

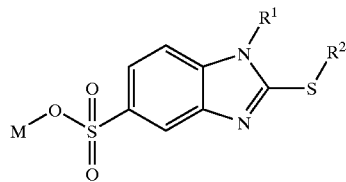

at least one compound represented by formula (II):

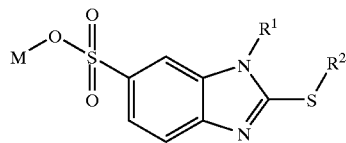

or a mixture of at least one compound represented by said formula (I) and at least one compound represented by said formula (II) as a surfactant, wherein M is hydrogen, an alkali atom or an ammonium group; $R^1$ is hydrogen, a —$(CH_2)_m$SO$_3$M group or a

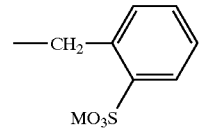

group; $R^2$ is an alkyl-, alkenyl- or alkynyl- group having 6 to 25 carbon atoms; and m is an integer between 1 and 5.

2. Photographic material according to claim 1, wherein said support is provided with at least one subbing layer or subbing layer system.

3. Photographic material according to claim 2, wherein at least one subbing layer or subbing layer system contains at least one compound represented by the above-mentioned formula (I), at least one compound represented by the above-mentioned formula (II) or a mixture of at least one compound represented by the above-mentioned formula (I) and at least one compound represented by the above-mentioned formula (II).

* * * * *